United States Patent [19]

Greschat et al.

[11] 4,176,280
[45] Nov. 27, 1979

[54] TOMOGRAPHIC X-RAY APPARATUS FOR PRODUCING TRANSVERSE LAYER IMAGES

[75] Inventors: Walter Greschat, Dormitz; Güenter Schwierz, Erlangen, both of Fed. Rep. of Germany

[73] Assignee: Siemens Aktiengesellschaft, Berlin & Munich, Fed. Rep. of Germany

[21] Appl. No.: 886,958

[22] Filed: Mar. 15, 1978

[30] Foreign Application Priority Data

Apr. 19, 1977 [DE] Fed. Rep. of Germany ....... 2717349

[51] Int. Cl.² .............................................. A61B 6/00
[52] U.S. Cl. .................................................. 250/445 T
[58] Field of Search .................................... 250/445 T

[56] References Cited

U.S. PATENT DOCUMENTS

| 3,778,614 | 12/1973 | Hounsfield | 250/445 T |
| 3,937,965 | 2/1976 | Vasseur | 250/445 T |
| 4,047,041 | 9/1977 | Houston | 250/445 T |

Primary Examiner—Alfred E. Smith
Assistant Examiner—T. N. Grigsby
Attorney, Agent, or Firm—Hill, Van Santen, Steadman, Chiara & Simpson

[57] ABSTRACT

In the illustrated embodiments, detectors for receiving a fan-shaped beam are arranged in one row with dimensions to resolve a layer of maximum extent, while further detectors of the same dimensions are arranged in one or more adjacent rows and staggered relative to the first row so that the several rows provide comparable resolution for a layer of minimum extent. Thus in generating a computer tomograph of a layer of small extent (as in the neck region), the successive rows of detectors are rendered sequentially responsive to the fan shaped beam. If a physically continuously rotating detector assembly is used with mechanical lateral shifting of the x-ray detector rows into the beam path interpolation can correct for any change in the angles of the ray paths for the respective rows. By converting the x-ray beam into corresponding electronic radiation, electronic switching to successive electron detector rows may be used, thereby maintaining essentially the same focus location for each row, even with continuous rotation.

6 Claims, 8 Drawing Figures

TOMOGRAPHIC X-RAY APPARATUS FOR PRODUCING TRANSVERSE LAYER IMAGES

BACKGROUND OF THE INVENTION

The invention relates to a tomographic apparatus for producing transverse layer images of a radiographic subject, with an x-ray measuring arrangement containing an x-ray source which produces a fan-shaped x-ray beam penetrating the radiographic subject, the cross-sectional extent of which perpendicular to the layer plane is equal to the layer thickness and in the layer plane is of a magnitude such that the entire radiographic subject is penetrated, and also containing a radiation receiver which determines the intensity of radiation behind the subject, and also with a drive device for the measuring arrangement for producing rotary movements and with a measured value converter for transforming the signals supplied by the radiation receiver into a layer image, the radiation receiver being composed of a number of individual detectors.

In a known tomographic apparatus of this type, the radiation receiver comprises a single row of detectors and the measuring arrangement is rotated through an angle of 360° to produce the input signals for the measured value converter. A tomographic apparatus of this type is suitable as a so-called entire-body scanner for photographing any desired transverse layer images. The detector row must be of such dimensions that the x-ray beam picked up by it fully permeates each body layer which is to be reproduced. The number of detectors should be determined in accordance with the largest body layer of which an image is to be made, and the image resolution required for this. In this instance, it is disadvantageous that when forming an image of a body layer which is substantially smaller than the maximum body layer, for example, a cross-section through the neck or the head of the patient, only a small number of detectors is operative for the production of the input signals for the measured value converter. The local resolution therefore decreases relative to the size of the body layer of which an image is to be formed.

SUMMARY OF THE INVENTION

The invention is based on the task of producing a tomographic apparatus of the type specified at the outset which provides good local resolution within a wide dimensional range of the body layer to be reproduced.

According to the invention, this task is solved in that the radiation receiver has two rows of detectors arranged adjacently and parallel to one another, the detectors of one detector row overlapping the detectors of the other detector row by approximately half the detector width, and in that there is a control device for the radiation receiver which enables the x-ray beam to be detected selectively by one detector row in each case. In the tomographic apparatus in accordance with the invention, where there are large body layers to be reproduced, only one detector row can be used. If the body layer to be detected is small then both detector rows can be used alternately to produce the input signals for the measured value converter. In this way the number of operative individual detectors is doubled in comparison with the use of only one detector row and the image resolution is of sufficiently good quality even in the case of small body layers. Coupled with the invention are the additional advantages that the scattered radiation can be picked up by the detectors not used for producing the input signals for the measured value converter, and that the scanning theorem can be satisified in the manner more fully explained in the detailed description with the aid of drawing illustrations.

The control device may be constructed such that it moves one row of detectors at a time mechanically into the x-ray beam. A further development of the invention consists in that the radiation receiver has an x-ray sensitive luminescent diode which is covered by a photocathode and which detects the entire x-ray beam, that opposite the photocathode are disposed the two detector rows which are composed of detectors for the electron beam issuing from the photocathode, and that an electron optics device is provided which selectively directs the electron radiation produced by the x-ray beam to one of the rows of detectors. In this embodiment no mechanical movement of the radiation receiver takes place.

The invention will be explained in greater detail hereinafter with reference to two exemplified embodiments illustrated in the accompanying drawings; other objects, features and advantages will be apparent from this detailed disclosure and from the appended claims.

DETAILED DESCRIPTION

Figure 1:
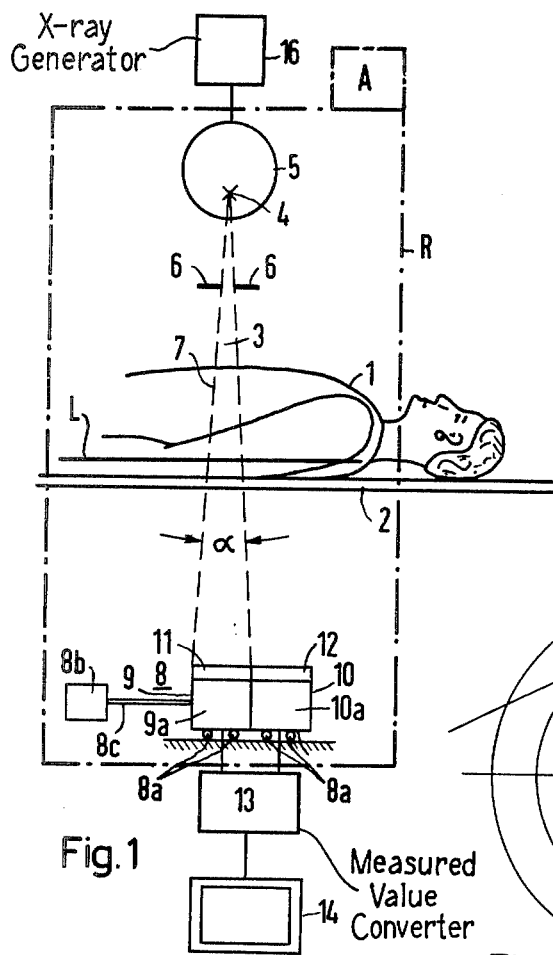
FIG. 1 shows a tomographic x-ray apparatus in accordance with the invention.
Figure 3:
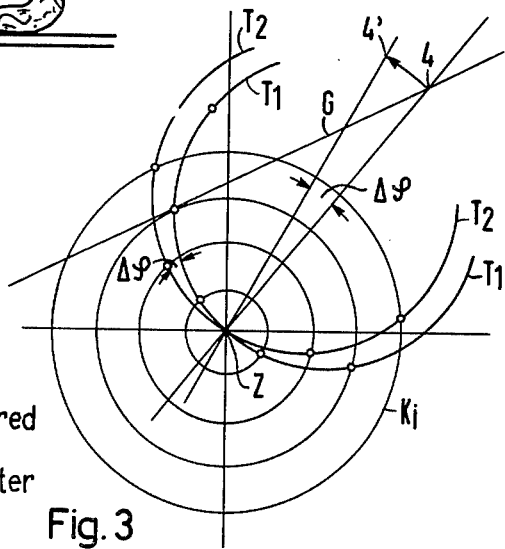
FIG. 3 shows a graphical illustration useful in explaining the method of obtaining the measuring signals.
Figure 2:
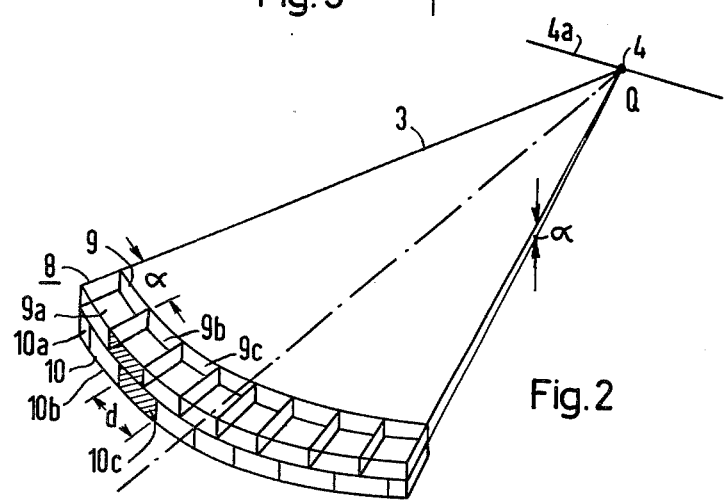
FIG. 2 shows the radiation receiver of the tomographic x-ray apparatus in accordance with FIG. 1 in perspective representation.

As shown in FIG. 1, a patient 1 is positioned on a couch 2 and is irradiated by an x-ray beam 3. The fan-shaped configuration of the beam 3 is best seen in FIG. 3. The x-ray beam 3 issues from the focal spot 4 of an x-ray tube 5 and is delineated by a primary radiation collimator 6 such that its cross-sectional extent perpendicular to the body layer 7 is generally equal to the layer thickness and, in the examined body layer 7, is of a size such that the entire patient cross section is permeated. Viewed in the direction of radiation, there is disposed behind the patient a radiation receiver 8 which consists of two rows of detectors, 9 and 10, arranged adjacently and parallel to one another, of which the detectors of the one detector row 9 overlap the detectors of the detector row 10 by approximately half the detector width d (FIG. 2). In front of each of the detectors 9a, 9b, etc. and 10a, 10b, etc. there is disposed a collimator. In FIG. 1 are illustrated schematically the collimators 11 and 12 of the detectors 9a and 10a.

The number of detectors 9a etc. and 10a etc. is selected according to the desired image resolution. Each detector row may be composed e.g. of 256 detectors. In FIG. 2, for the sake of clarity, only a few of these detectors are illustrated. FIG. 2 clearly shows the aperture angle of the x-ray beam as determined by the rectangular aperture of the primary radiation diaphragm plates 6.

To scan the patient 1, and more particularly the body layer 7, the measuring arrangement 5, 8 is rotated about the patient through 360°. If a relatively large body layer is to be examined, for example in the abdominal area of the patient, only one of the detector rows, more particularly the detector row 9, is used to form the measuring signals. The scanning may in this instance be effected in such a manner that, for example, the x-ray tube 5 is pulsated once per angle degree so that where there are 256 detectors per detector row, 256×360 measuring signals are supplied to a measured value converter 13 in one scanning operation. The measured value converter 13 contains a computer which computes an image of the irradiated body layer from the measured value signals. The measured value converter 13 is connected to a video apparatus 14 for reproduction of this image. The x-ray tube 5 is connected to an x-ray generator 16 which supplies the required high voltage.

In the described mode of operation of the tomographic apparatus the detector row 10 can be used to pick up the scattered radiation issuing from the patient 1. The output signals of the detector row 10 can be used in the measured value converter 13 to correct the measured value signals of the detector row 9. During a scanning operation the detector row 9 in fact picks up the scattered radiation as well as the primary x-radiation, i.e. the x-ray beam 3. The scattered radiation picked up by the detector row 9 is in this instance practically equal to the scattered radiation picked up by the detector row 10. Correction is thus possible by the signals of the detector row 10 being subtracted from the corresponding signals of the detector row 9.

If a small body layer, for example in the neck or head region of the patient 1, is to be scanned, then the detector row 10 is also used to produce measured value signals. This can take place in such a manner that per angle position of the measuring arrangement 5, 8, measured value signals are produced, initially be means of the detector row 9 and then by means of the detector row 10, by firstly the detector row 9, and subsequently the detector row 10 picking up the x-ray beam 3 which issues from the patient 1. For this purpose there may be provided a mechanical control device which shifts the detector row 9 from the position shown in FIG. 1, out of the x-ray beam 3, and moves the detector row 10 into this x-ray beam 3, i.e. moves this to the position of the detector row 9. The course of a scanning procedure of the examined body layer of the patient 1 may thus be effected in that at each angle-position the primary radiation is measured initially with the detector row 9 and then with the detector row 10. In this instance, compared with the use of a single row of detectors, due to the mutually offset arrangement of the detectors 9 and 10, twice the number of detectors is operative. A good resolution is therefore provided even with small body layers.

It is also conceivable within the scope of the invention to rotate the measuring arrangement 5, 8, continuously about the patient 1 through 360° to scan a body layer. In this rotation, the displacement of the detector rows 9 and 10 can take place periodically. This displacement is, of course, as in the previously described instance, a tilting movement about the straight line 4a, FIG. 2, which extends through the focus 4. Since in the last described case after a displacement the focus 4 has advanced relative to the preceding measurement, a correction is necessary. This correction is possible by way of a one-dimensional interpolation of the measured values of a detector row.

This is described hereinafter with reference to FIG. 3. If the measured values at the feet of the perpendicular from the center of rotation Z are plotted on the integration line G (path of the x-radiation), then the measured values appear on the circle of Thales through the center of rotation Z and the focus 4. On rotation of the measuring arrangement 5, 8, through angle $\alpha\phi$ the Thales circle rotates about Z through the same angle. The more densely the detectors are arranged in a detector row, the more closely the measured values, indicated by dots, lie on its Thales circle. It is necessary to obtain as uniform a coverage of the plane in the layer region as possible with these measuring points. On rotation of the focus through the angle $\alpha\phi$ about the center of rotation Z into the position 4′, and on measuring with the other detector row, the measured values are no longer obtained on the Thales circle $T_1$, on which all the measured values in the original position of the focus 4 lie, but on the Thales circle $T_2$ which has been rotated through $\alpha\phi$. The spatial interval between the circles $K_i$, on which the measured values of the i-th detector element lie, are, however, equidistant, so that only a one-dimensional interpolation on every second circle has to be effected in order to obtain the measured values on the desired Thales circle $T_1$.

Figure 4:
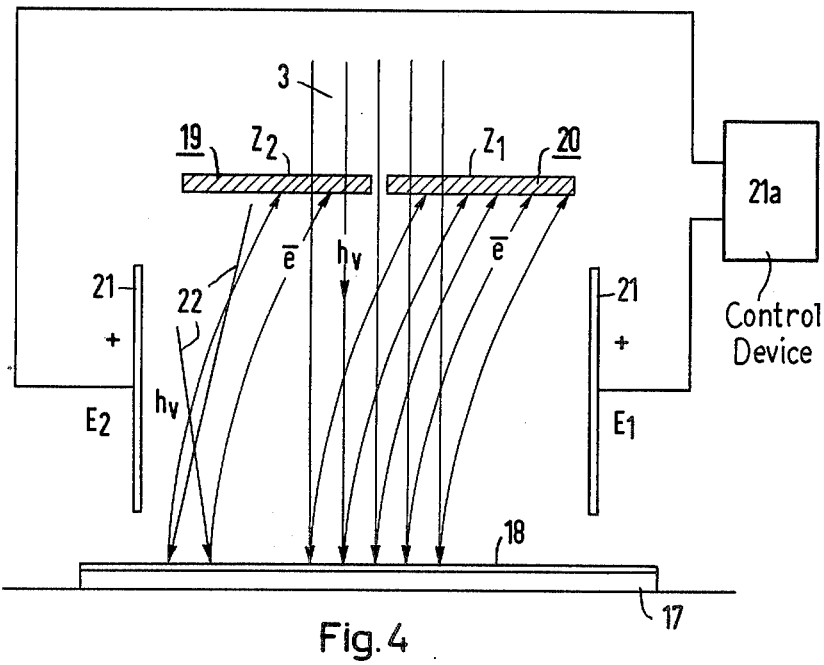
FIG. 4 shows another embodiment of the radiation receiver of an x-ray examination apparatus in accordance with the invention.

In FIG. 4 there is illustrated an exemplified embodiment for the radiation receiver wherein the radiation receiver has a luminescent diode 17 which is covered by a photocathode 18. In this instance the entire x-ray beam 3 strikes the luminous layer 17. The radiation receiver has two detector rows 19 and 20 which correspond to the detector rows 9 and 10 and lie opposite the photocathode 18. The individual detectors of the detector rows 19 and 20 are also disposed in an overlapping longitudinally offset manner. The detector rows 19 and 20 pick up the electron radiation issuing from the photocathode 18. There is provided an electron optics device 21 which is connected to a control device 21a which causes the electron radiation which issues from the photocathode 18 to selectively impinge upon either the detector row 19 or the detector row 20.

FIG. 4 illustrates that the electron radiation produced by the primary x-ray beam 3 strikes the detector row 20 and the electron radiation produced by the scattered radiation 22 strikes the detector row 19. To effect a change-over of the detector rows so as to interchange their measurement functions, the voltage at the electron optics device 21 must be changed.

In a radiation receiver in accordance with FIGS. 1, 2 and 4, the scanning theorem is satisfied and thus interference effects arising from too coarse a scanning are avoided if the two detector rows are used alternately for detecting the primary x-radiation. This is explained in more detail hereinafter with reference to FIGS. 5 to 8.

Figure 5:
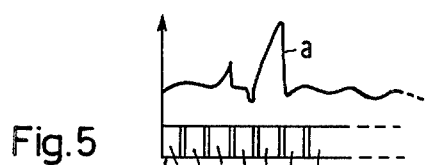
FIGS. 5 to 8 show illustrations in explanation of the invention in conjunction with the scanning theorem.

FIG. 5 shows a curve a which reproduces the variation in intensity in the x-radiation in front of a radiation receiver 22 which is formed by a single detector row. The radiation receiver 22 is partially illustrated in FIG. 5. In FIG. 5 are shown the individual detectors 26 to 32 of the radiation receiver 22.

The radiation detector 22 averages the intensity curve a, i.e. each detector 26 to 32 etc. averages the radiation over its input surface. The output signal of the individual detectors 26 to 32 etc. is thus coordinated with predetermined points of the averaged curve b in accordance with FIG. 6. These points are designated by 33 to 38 in FIG. 6.

Since the output signals of the detectors 26 to 32 etc. only reproduce the points 33 to 38 etc. of the averaged curve b, the scanning theorem is determinative for judging whether the original curve a can be formed from these output signals. The scanning theorem states that a curve can be reconstructed from selected curve points if no higher frequencies than twice the point sequence frequency are contained in the frequency spectrum of the curve. To check, it was assumed that higher frequencies are contained in the original curve a. The averaging over the detector surface is effected in accordance with the window function illustrated in FIG. 7, which shows the transmission of a single detector as a function of the local frequency. If the width of the individual detectors 26 to 32 etc. is equal, i.e. d, (see FIG. 2), the first zero passage of the window function in accordance with FIG. 7 lies at the point 39 at (1/d). The local scanning frequency, however, is only (1/d). One band of the local frequency (1/d) is filtered out from the original curve a, taking into consideration the filter function in accordance with FIG. 7 only up to the first zero passage. To satisfy the scanning theorem, however, the zero passage would have to lie at (1·1)/(2·d). It therefore follows that the original curve a cannot be reconstructed exactly from the output signals of the individual detectors 26 to 32 etc. with a single detector row as radiation receiver.

Figure 8:
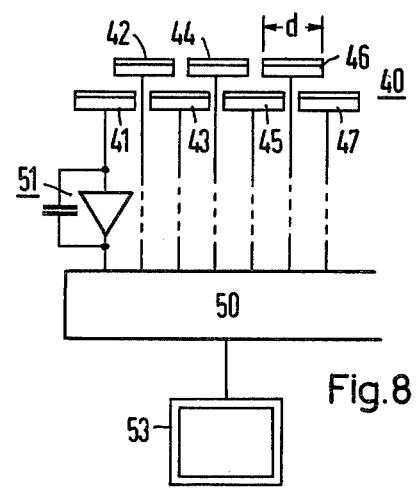

FIG. 8 shows a radiation receiver 40 which corresponds in principle to the radiation receiver 8 or the detector rows 19, 20, FIG. 4. According to FIG. 8 the radiation receiver 40 is composed of a row of single detectors 41, 42, 43 etc. which are arranged such that they overlap one another. Between the outputs of the detectors 41 etc. and a computer 50 there lie integrators 51, only one of which is illustrated in FIG. 8. The integrators 51 each hold the output signal of the respective detector until it has been taken over by the computer 50, the signal then being erased to restore the integrator to its initial condition. The interrogation of the output signals of the integrators 51 is effected by the computer 50 such that the output signals of the integrators 51 are read out successively so that the original curve a in accordance with FIG. 2 can be reconstructed from the measured values scanning with double the signal frequency. It is therefore essential that the output pulses of the integrators 51 etc. are interrogated successively, the step width of the scanning corresponding to half the length over which the original intensity distribution has been averaged by the detectors.

The radiation receiver 40 is illustrated in FIG. 8 viewed from above, having reference to the basic orientation of FIG. 1.

Figure 6:
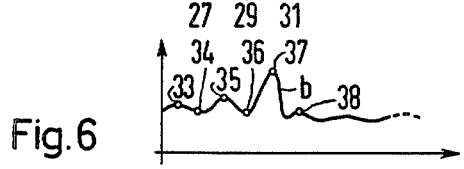
Figure 7:
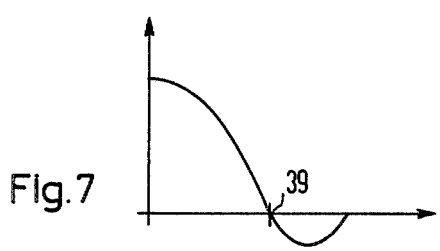

The curves in FIGS. 5 and 6 are obviously only intended as examples.

In the exemplified embodiment in accordance with FIG. 1 it is further illustrated that the radiation receiver 8 is displaceably mounted on rollers 8a, so that the detector row 9 or 10 can be moved selectively into the x-ray beam 3 by a control device 8b, for example an electromagnet, by way of a rod 8c.

FIG. 1 schematically illustrates a frame R which carries the x-ray measuring arrangement 5, 8, and which is capable of rotation by means of a drive mechanism A about a longitudinal axis L for the purpose of scanning the patient lying on the couch 2.

It will be apparent that many modifications and variations may be effected without departing from the scope of the novel concepts and teachings of the present invention.

We claim as our invention:

1. Tomographic apparatus for producing transverse layer images of a radiographic subject, comprising an x-ray measuring arrangement including an x-ray source which produces a fan-shaped x-ray beam which penetrates the radiographic subject, the cross-sectional extent of which perpendicular to the layer plane is generally equal to the layer thickness, and a radiation receiver which determines the intensity of radiation behind the subject; and a drive device for the measuring arrangement for producing rotary movements, and a measured value converter for transforming the signals supplied by the radiation receiver into a layer image, the radiation receiver being composed of a number of individual detectors, characterized in the radiation receiver (8, 17 to 20) having two or more detector rows (9, 10; 19, 20) arranged adjacent and parallel to one another, the detectors (9a etc.) of one detector row (9, 19) overlapping the detectors (10a etc.) of the other detector row (10, 20) by approximately half the detector width (d), and a control device (8b, 21, 21a) for the radiation receiver (8, 17 to 20) for actuating the same to selectively respond to the x-ray beam (3) by way of one of the detector rows (9, 10, 19, 20) in each instance.

2. Apparatus according to claim 1, characterized in the control device (8b) being constructed such that it mechanically moves one detector row at a time (9, 10) into the x-ray beam (3).

3. Apparatus according to claim 2, characterized in the control device, (8b) being constructed such that it moves the radiation receiver (8) periodically back and forth to sequentially place the detector rows (9, 10) in the x-ray beam (3).

4. Apparatus according to claim 3, characterized in that the movements of the radiation receiver (8) and the drive device for the measuring arrangement (5, 8) for rotating the measuring arrangement (5, 8) are coordinated with one another such that the measuring arrangement (5, 8) is rotated through discrete angles and in each angle position each detector row (9, 10) is moved into the x-ray beam (3).

5. Apparatus according to claim 3, characterized in that the movements of the radiation receiver (8) and the drive device for the measuring arrangement (5, 8), for rotation of the measuring arrangement (5, 8), are coordinated to one another such that the measuring arrangement (5, 8) is continuously rotated and at the same time the periodic movement of the radiation receiver (8) takes place, and that there are coordinated with the measured value converter (13) means for correction of the measured value signals corresponding to the movement of the x-ray source (5) between the times of obtaining two sets of measured value signals from the radiation receiver (8).

6. Apparatus according to claim 1, characterized in the radiation receiver having a luminescent layer (17) for detecting the entire x-ray beam (3), a photocathode (18) covering the luminescent layer (17), two detector rows (19, 20) being opposite the photocathode (18), said two detector rows (19, 20) comprising detectors for the electron radiation issuing from the photocathode (18), and an electron optics device (21) operative to selectively direct the electron radiation produced by the x-ray beam (3) to one detector row (19, 20) respectively.

* * * * *